(12) United States Patent
Lessley et al.

(10) Patent No.: US 9,908,137 B2
(45) Date of Patent: Mar. 6, 2018

(54) FLUID APPLICATION DEVICE HAVING A MODULAR NON-CONTACT NOZZLE FOR APPLYING FLUID TO AN ARTICLE

(71) Applicant: Illinois Tool Works Inc., Glenview, IL (US)

(72) Inventors: Mel Steven Lessley, Villa Hills, KY (US); Edward Wayne Bolyard, Jr., Old Hickory, TN (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 194 days.

(21) Appl. No.: 14/525,498

(22) Filed: Oct. 28, 2014

(65) Prior Publication Data
US 2015/0132481 A1     May 14, 2015

Related U.S. Application Data

(60) Provisional application No. 61/904,317, filed on Nov. 14, 2013.

(51) Int. Cl.
    B05C 5/02         (2006.01)
    B05D 1/02         (2006.01)
    (Continued)

(52) U.S. Cl.
    CPC ...... B05C 5/0245 (2013.01); A61F 13/15609 (2013.01); B05B 1/005 (2013.01);
    (Continued)

(58) Field of Classification Search
    CPC ..... B05C 5/0245; B05C 5/027; B05C 5/0241; B05C 13/00; B65H 57/16; B65H 57/04;
    (Continued)

(56) References Cited

U.S. PATENT DOCUMENTS 3,529,571 A     9/1970    Good et al.
3,997,128 A    12/1976    Hara et al.
(Continued)

FOREIGN PATENT DOCUMENTS

CN        1380050 A     11/2002
CN    101657265 A      2/2010
(Continued)

OTHER PUBLICATIONS

International Search Report for PCT/US2014/065246 dated Feb. 5, 2015.
(Continued)

*Primary Examiner* — Laura Edwards
(74) *Attorney, Agent, or Firm* — Levenfeld Pearlstein, LLC

(57) ABSTRACT

A fluid application device, a nozzle assembly and a method of applying a fluid onto a strand of material provided. The fluid application device includes an applicator head and a nozzle assembly. The nozzle assembly includes a guide slot for receiving a strand of material. The nozzle assembly further includes an orifice, spaced from the guide slot, configured to discharge a first fluid to onto the strand, and at least one outlet, adjacent to the orifice, for discharging a second fluid to act on the first fluid. The method includes positioning the strand at the closed end of the guide slot so that the strand is spaced a predetermined distance from the orifice, feeding the strand through the guide slot at a predetermined speed, applying the first fluid onto the strand from the orifice and discharging the second fluid from the at least one outlet.

17 Claims, 5 Drawing Sheets

(51) Int. Cl.
*B05B 1/00* (2006.01)
*B65H 57/04* (2006.01)
*B65H 57/16* (2006.01)
*A61F 13/15* (2006.01)
*B65H 57/00* (2006.01)
*B05C 13/00* (2006.01)

(52) U.S. Cl.
CPC ............ *B05C 5/027* (2013.01); *B05C 5/0241* (2013.01); *B05D 1/02* (2013.01); *B65H 57/00* (2013.01); *B65H 57/04* (2013.01); *B65H 57/16* (2013.01); *B05C 13/00* (2013.01); *B65H 2701/31* (2013.01)

(58) Field of Classification Search
CPC .... B65H 2701/31; B65H 57/00; B05B 1/005; A61F 13/15609; B05D 1/02
USPC ................ 118/63, 314, 325, 420, 428, 307; 425/463, 466; 239/290, 294, 270, 298; 156/62.4, 578
See application file for complete search history.

(56) References Cited

U.S. PATENT DOCUMENTS

| | | | |
|---|---|---|---|
| 5,289,767 A | 3/1994 | Montalto et al. | |
| 5,389,151 A | 2/1995 | Fort | |
| 6,001,178 A | 12/1999 | Borgmann | |
| 6,361,634 B1 * | 3/2002 | White | A61F 13/15593 156/161 |
| 6,368,409 B1 | 4/2002 | Borsuk et al. | |
| 6,540,831 B1 | 4/2003 | Craine et al. | |
| 6,619,566 B2 | 9/2003 | Gressett et al. | |
| 8,033,243 B2 * | 10/2011 | Bolyard, Jr. | B65H 57/04 118/305 |
| 2002/0136833 A1 | 9/2002 | Riney | |
| 2004/0164180 A1 | 8/2004 | Harris et al. | |
| 2005/0274318 A1 | 12/2005 | Bolyard et al. | |
| 2009/0000545 A1 | 1/2009 | Bolyard et al. | |
| 2010/0024987 A1 | 2/2010 | Saine et al. | |
| 2010/0025514 A1 | 2/2010 | Kipping et al. | |
| 2012/0258246 A1 | 10/2012 | Saine et al. | |

FOREIGN PATENT DOCUMENTS

| | | |
|---|---|---|
| CN | 101678990 A | 3/2010 |
| EP | 1176232 A1 | 1/2002 |
| EP | 1243347 A2 | 9/2002 |

OTHER PUBLICATIONS

International Search Report for PCT/US2014/065250 dated Feb. 5, 2015.

International Search Report for PCT/US2014/065484 dated Mar. 19, 2015.

\* cited by examiner

FLUID APPLICATION DEVICE HAVING A MODULAR NON-CONTACT NOZZLE FOR APPLYING FLUID TO AN ARTICLE

BACKGROUND

The following description relates to a fluid application device having a modular nozzle for applying a fluid to a moving article, and in particular, having a modular non-contact nozzle for applying an adhesive to one or more strands of material.

Nonwoven fabrics are engineering fabrics that provide specific functions such as absorbency, liquid repellence, resilience, stretch, softness, strength, flame retardant protection, easy cleaning, cushioning, filtering, use as a bacterial barrier and sterility. In combination with other materials, nonwoven materials can provide a spectrum of products with diverse properties and can be used alone or as components of hygiene apparel, home furnishings, health care, engineering, industrial and consumer goods.

A plurality of elasticated strands may be positioned on and bonded to the nonwoven materials to, for example, allow for flexibility fitting around an object or a person. The strands may be bonded to the nonwoven fabric with an adhesive in the form of a glue fiber. In one configuration, the strands are fed past a nozzle on an adhesive application device. The nozzle may include a plurality of outlets through which the glue fiber may be discharged. A second fluid, such as air, may be discharged through separate outlets to control the application of the glue fiber such that the glue fiber is vacillated across the respective strands as the strands pass by the nozzle. In particular, the outlets for discharging air may be positioned on opposite sides of the outlet for discharging the glue fiber, such that there are two air discharge outlets for each glue discharge outlet. In this configuration the strands are spaced approximately 5-8 millimeters (mm) from respective discharge outlets of the nozzle. That is, the glue fiber is discharged over a gap of approximately 5-8 mm to be applied to the strands.

However, as a result of the distance between the discharge outlets and the strands, it is difficult to ensure the discharged glue fiber is adequately received on the strands. In addition, it may be difficult to ensure that the strands are positioned at a location where adhesive may be most efficiently applied thereto. Thus, a portion of the discharged glue fiber may be discharged past the strands rather than applied to the strands. This condition is commonly referred to as overspray. Overspray results in inefficient application of glue to the strands such that a portion of the discharged glue goes unused. In turn, increased material costs may result. In addition, glue application patterns may not be accurately controlled, causing increased creep in the final products. Further, to achieve an acceptable glue coating on the strands, the speed at which the strands are fed past the nozzle should not exceed 400 meters per minute (mpm).

Accordingly, it is desirable to provide a fluid application device having a modular nozzle that may apply a fluid, such as an adhesive, in a non-contacting manner, to a moving article at higher speeds while decreasing overspray.

SUMMARY

According to one aspect, there is provided a fluid application device comprising an applicator head and a nozzle assembly fluidly coupled to the applicator head. The nozzle assembly includes a guide slot configured to receive a strand of material. The guide slot includes an open end and a closed end. The nozzle assembly also includes an orifice spaced from the guide slot, the orifice configured to discharge a first fluid onto the strand, and at least one outlet adjacent to the orifice, the at least one outlet configured to discharge a second fluid to act on the first fluid. The closed end of the guide slot defines a stop configured to space the strand a predetermined distance from the orifice such that the first fluid is discharged from the orifice over the predetermined distance onto the strand.

According to another aspect, there is provided a nozzle assembly of a fluid application device for applying at least one fluid to a strand of material. The nozzle assembly includes a guide plate having a guide slot configured to receive a strand of material, the guide slot having an open end and a closed end. The nozzle assembly also includes an orifice configured to discharge a first fluid onto the strand of material, and at least one outlet positioned adjacent to the orifice configured to discharge a second fluid to control application of the first fluid onto the strand. The guide slot is spaced from the orifice in a direction of travel of the strand. The closed end of the guide slot defines a stop configured to space the strand a predetermined distance from the orifice such that the first fluid is discharged from the orifice over the predetermined distance onto the strand According to still another aspect, there is provided a method of applying a fluid with a nozzle assembly to a stand of material, the nozzle assembly including a guide slot configured to receive the article passing therethrough. The guide slot includes an open end and a closed end. The nozzle assembly further includes an orifice spaced from the closed end and configured discharge a first fluid therefrom and at least one outlet configured to discharge a second fluid therefrom. The method includes positioning the article at the closed end of the guide slot so that the article is spaced a predetermined distance from the orifice, feeding the article through the guide slot at a predetermined speed, and applying the first fluid to the article from the orifice over the predetermined distance. The method further includes discharging the second fluid from the at least one outlet to control application of the first fluid onto the strand.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
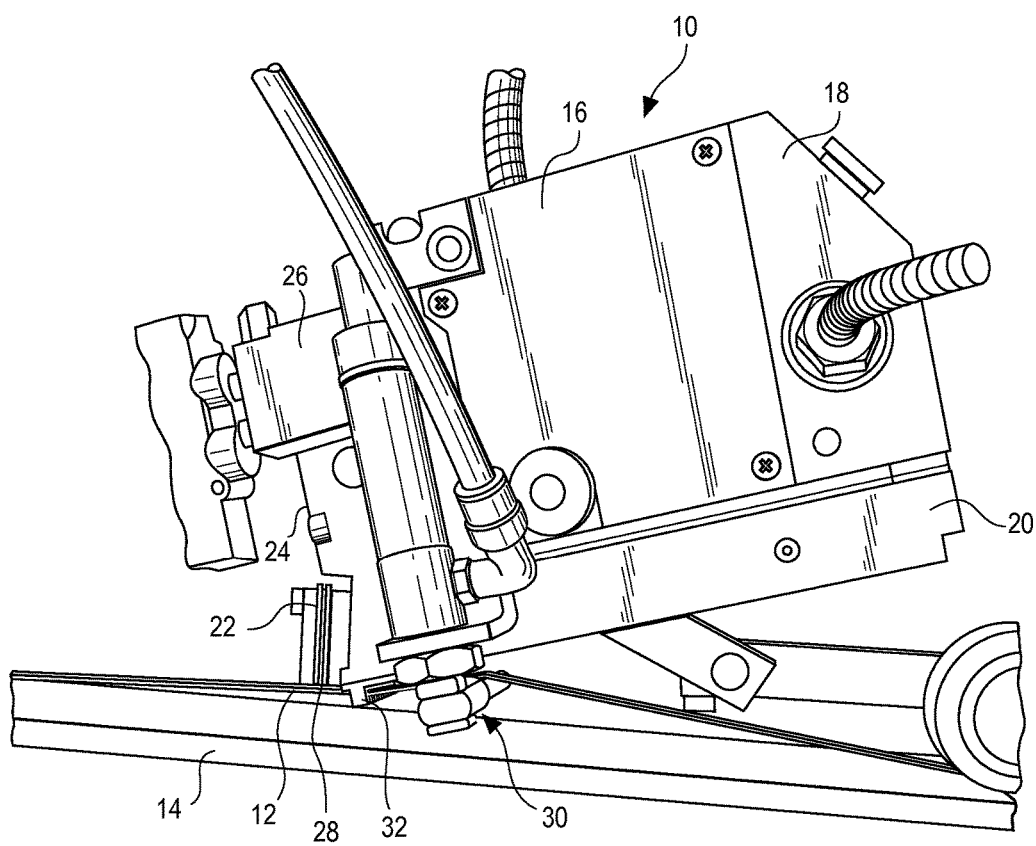
FIG. 1 is a perspective view of a fluid application device having a non-contact nozzle assembly according to an embodiment of the present invention.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is a perspective view of a fluid application device 10 according to an embodiment of the present invention. The fluid application device 10 may be used to apply a fluid on an article. For example, the fluid application device 10 may apply a first fluid F1 (see FIG. 2) on an article. The first fluid F1 may be a viscous fluid that is a liquefied material heated or non-heated between 10 and 50,000 centipoise (cps). The first fluid F1 may be, for example, an adhesive, and the article may be, for example, an elastic or non-elastic strand 12 of material. That is, in one embodiment, the fluid application device 10 is part of a strand coating system. The adhesive may be applied to the strand 12 so that the strand 12 may be adhered to a substrate 14, such as a nonwoven material. The strand 12, in one embodiment, may be made from an elastic material and may be in either a stretched condition or a relaxed condition as the first fluid F1 is applied. The strand 12 of material may be, for example, spandex, rubber or other similar elastic material.

According to one embodiment of the present invention, the fluid application device 10 includes an applicator head 16. The applicator head 16 may include a first fluid supply unit 18, a second fluid supply unit 20 and a nozzle assembly 22. The first fluid supply unit 18 is configured to receive the first fluid F1 from a first fluid F1 source (not shown) and the second fluid supply unit 20 is configured to receive a second fluid F2 (shown in FIG. 2) from a second fluid source (not shown). The nozzle assembly 22 is fluidly coupled to, i.e., is in fluid communication with, the first fluid supply unit 18. The nozzle assembly 22 may also be fluidly coupled to, i.e., may be in fluid communication with, the second fluid supply unit 20. Accordingly, the nozzle assembly 22 may receive the first fluid F1 from the first fluid F1 supply unit 18 and the second fluid F2 from the second fluid supply unit 20.

In some embodiments, the applicator head 16 may also include an adapter 24 secured to at least one of the first fluid supply unit 18 and second fluid supply unit 20. The adapter 24 is positioned adjacent to the nozzle assembly 22 and is fluidly coupled to, i.e., is in fluid communication with, the nozzle assembly 22. In addition, the adapter 24 is fluidly coupled to one of or both of the first fluid supply unit 18 and second fluid supply unit 20, such that the nozzle assembly 22 may receive the first fluid F1 and the second fluid F2 via the adapter 24. That is, the adapter 24 is in fluid communication with at least one of the first fluid supply unit 18 and the second fluid supply unit 20 and also the nozzle assembly 22. The adapter 24 is configured to have the nozzle assembly 22 secured thereto such that the nozzle assembly 22 may be properly positioned and oriented relative to the applicator head 16 for application of the first fluid F1 onto the strands 12. It is understood that the present disclosure is not limited to this configuration and that the nozzle assembly 22 may be secured to the applicator head 16, adapter 24 or other adjacent component of the applicator head 16.

The applicator head 16 may also include a flow control module 26. The flow control module 26 may include a valve or series of valves to regulate a flow of the first fluid F1 and second fluid F2 from the first fluid supply unit 18 and second fluid supply unit 20, respectively, to the nozzle assembly 22. In some embodiments, the adapter 24 and flow control module 26 are implemented as the same unit. This unit provides an adhesive path between one of or both of the first and second fluid supply units 18, 20 and the nozzle assembly 22. This unit, i.e., the combined adapter 24 and flow control module 26 may also include valving to start and stop the flow of adhesive.

Figure 2:
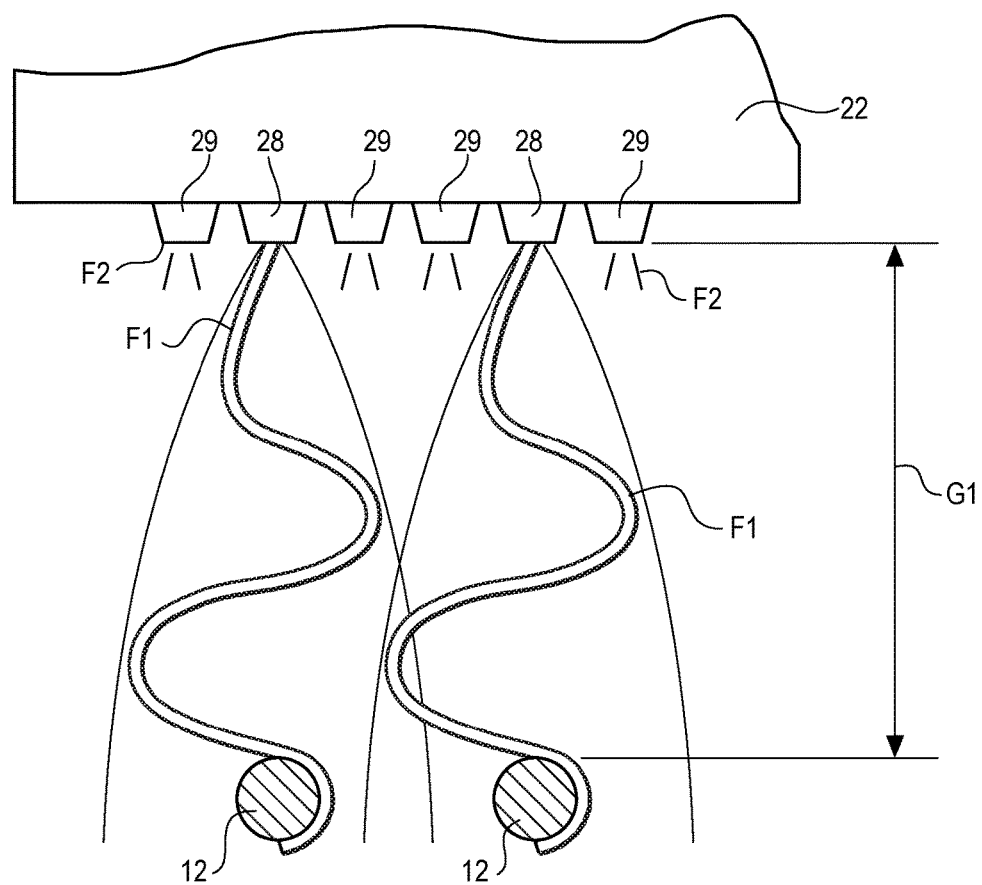
FIG. 2 is a front view of a non-contact nozzle assembly of a fluid application device according to an embodiment of the present invention.

FIG. 2 is a front view of the nozzle assembly 22 according to an embodiment of the present invention. Referring to FIG. 2, the nozzle assembly 22 includes at least one orifice 28. The first fluid F1 may be discharged through the orifice 28 to be applied on the strand 12. The orifice 28 may be approximately 0.016 in.-0.02 inches (in.) wide, but is not limited thereto. For example, the width of the orifice 28 may vary to accommodate different sizes of strands 12. It is understood that the width of the orifice 28 may refer to a diameter in embodiments where the orifice 28 is circular in shape, or the width measured across a center point of a non-circular shape, such as square or rectangular, in other embodiments. There may be at least one orifice 28 associated with each strand 12 of material. In some embodiments, there is one orifice 28 associated with each strand 12. That is, each orifice 28 may discharge the first fluid to a respective strand 12.

As noted above, the first fluid F1 may be an adhesive, such as a hot melt adhesive. The adhesive may be discharged from the orifice 28 as a filament or fiber to be applied on the strand 12. The first fluid is discharged over a gap G1 between the orifice 28 and the strand 12. In one embodiment, the gap G1 may be 0-3 mm, and preferably, 1-2 mm, or in another embodiment, 0-2 mm. The first fluid F1 may be discharged from the orifice 28 as a substantially continuous filament or fiber, but may be intermittently discontinuous so long as the first fluid F1 is sufficiently applied to the strand 12 to allow the strand 12 to satisfactorily bond to the substrate 14. The applicator head 16 may be heated to either melt the first fluid F1 or maintain the first fluid F1 in a melted condition. For example, the first fluid supply unit 18, the second fluid supply unit 20, and/or the nozzle assembly 22 may be heated, and thus, may also radiate heat outwardly. The applicator head 16 may also include a heater.

The nozzle assembly 22 may also include at least one outlet 29 configured to discharge the second fluid F2. The second fluid F2 may be, for example, air, and may be used to control the application of, or otherwise act on the first fluid to vary a discharge path of the first fluid during application onto the strand 12. For example, the second fluid may oscillate the first fluid as it is applied. Accordingly, the first fluid may be applied on the strand 12 in a desired pattern.

There may be anywhere from one to six air outlets 29 associated with each orifice 28 used to control or alter the discharge of the first fluid F1 from the orifice 28. Preferably, more than one outlet 29 is associated with each orifice 28. The outlets 29 and orifices 28 may be positioned along a common plane or line. Alternatively, the outlets may be positioned along a separate line or plane than the orifices 28. In one embodiment, there are at least two outlets 29 configured to discharge the second fluid F2 adjacent to each orifice 28 that discharges the first fluid F1. The second fluid F2 may be discharged from the outlets 29 adjacent to each orifice 28 to cause the first fluid F1 to oscillate and be applied to the strand 12 in the desired pattern. For example, the first fluid F1 may be applied to the strand 12 in a substantially sinusoidal pattern. However, the present disclosure is not limited to this configuration, and the first fluid F1 may be applied in other patterns. For example, the first fluid may be vacillated or oscillated by the second fluid such that the first fluid is applied in, for example, repeated, non-repeated, irregular and/or asymmetrical pattern or patterns. In some examples, the second fluid F2 may be alternately discharged from outlets 29 adjacent to an orifice 28. That is, discharge of the second fluid F2 may be controlled to be started and stopped in an alternating, or partially overlapping manner between the outlets 29, or may be continuously supplied from the outlets 29. As noted above, the first fluid F1 may be continuously or intermittently discharged from the orifice 28. When the first fluid F1 is applied to the strand 12 with assistance or under control of the second fluid F2, a continuous stream of the first fluid F1 may be broken apart by the second fluid F2 such that the first fluid F1 is applied on the strands intermittently.

Figure 3:
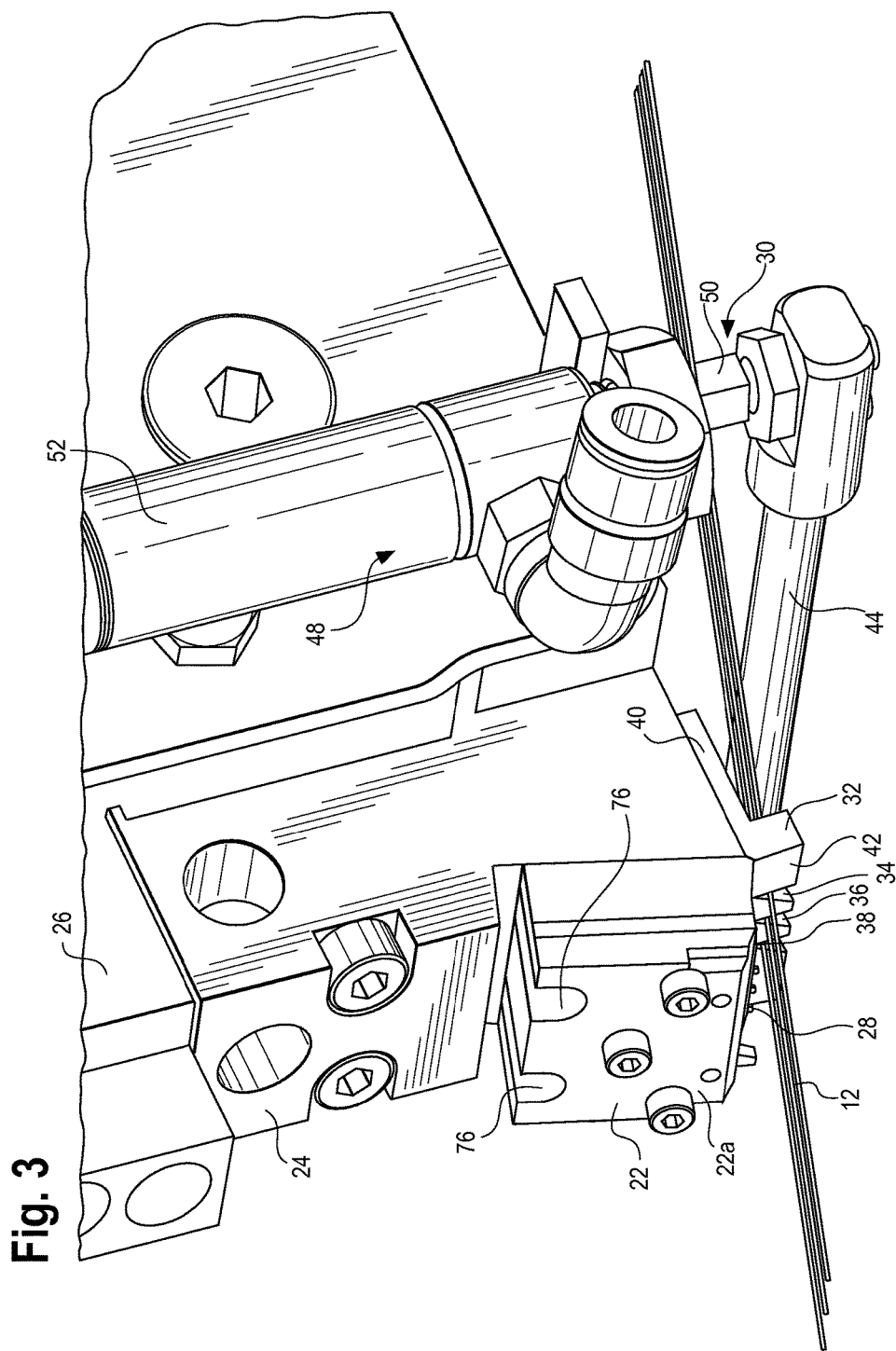
FIG. 3 is a perspective view of a fluid application device having a non-contact nozzle assembly according to an embodiment of the present invention.

FIG. 3 is a perspective view of the fluid application device 10 according to an embodiment of the present invention. Referring to FIGS. 1 and 3, the fluid application device 10 further includes a strand engagement device 30. The strand engagement device 30 may be formed integrally with the applicator head 16. Alternatively, the strand engagement device 30 may be secured to the applicator head 16 or other component of the fluid application device 10 with a suitable fastener, including, but not limited to, bolts, screws, rivets, adhesives, welds and the like. The strand engagement device 30 is configured to engage the strands 12 and move the strands 12 toward or away from the applicator head 16 and nozzle assembly 22 based on a line condition (active or static) of the fluid application device 10, as discussed further below.

Referring still to FIGS. 1 and 3, the nozzle assembly 22 includes a guide plate 32 to assist in positioning of the strands 12 relative to the orifices 28 and outlets of the nozzle assembly 22. The guide plate 32 includes at least one guide slot 34 through which the strand 12 may be fed. The guide slot 34 may be formed in a substantially inverted v-shape, with an open end 36 of guide slot 34 corresponding to a wide portion of the inverted v-shape, and a closed end 38 of the guide slot correspond to a narrow portion of the inverted v-shape. The closed end 38 may act as a limit or stop for the strand 12 to position the strand 12 at the desired position relative the orifice 28 and outlets for application of the first fluid F1. That is, the closed end 38 may act as a stop to position the strand 12 a predetermined distance, or gap G1, from the orifice 28. The strand 12 may either contact the closed end 38 or be positioned in close proximity to the closed end 38. The predetermined distance, or gap G1, between the strand 12 and orifice 28 is a distance or gap where overspray may be reduced or minimized. In a direction of travel of the strands 12, the at least one guide slot 34 may be positioned before the orifices 28 of the nozzle assembly 22.

According to one embodiment of the present invention, the at least one guide slot 34 may include three guide slots 34. However, it is understood that the number of guide slots 34 may vary, and is not limited to the example above. Each guide slot 34 is associated with a corresponding orifice 28 of the nozzle assembly 22. That is, each guide slot 34 is substantially aligned with a corresponding orifice 28 of the nozzle assembly. For example, the closed end 38 of respective guide slots 34 may be aligned with respective orifices 28 in the direction of travel of the strands 12. Each guide slot 34 is configured to receive a separate strand 12, although it envisioned that more than one strand 12 may be received in each guide slot 34.

In one embodiment, the nozzle assembly 22 includes a body portion 22a and the guide plate 32 is formed separately from the body portion 22a. The guide plate 32 may be formed by a first flange 40 secured to the adapter 24 and a second flange 42 depending from the first flange 40. The at least one guide slot 34 may be formed in the second flange 42. The guide plate 32 may be secured to the adapter 24 using known fastening techniques, and may be removed, independently of the body portion 22a, for replacement and/or servicing. Alternatively, the guide plate 32 may be formed integrally with the body portion 22a of the nozzle assembly 22. For example, the guide plate 32 may include a flange that depends from the body portion 22a in which the guide slots 34 are formed. In another embodiment, the guide plate 32 may be removably secured to the nozzle assembly 22. That is, in one embodiment, the guide plate 32 may be formed integrally with the nozzle assembly 22 by being selectively releasably secured to the body portion 22a of the nozzle assembly 22. For example, the guide plate 32 may be directly secured to the body portion 22a using a known suitable fastener or fasteners. Accordingly, the guide plate 32 may be removed from the nozzle assembly 22, independent of the body portion 22a for replacement or service.

With further reference to FIG. 3, the strand engagement device 30 includes an engagement arm 44 configured to support and/or guide the strand or strands 12. The engagement arm 44 is adjustable to move the strands 12 within respective guide slots 34 to accurately position the strands 12 relative to the respective orifices 28 and outlets.

Figure 4:
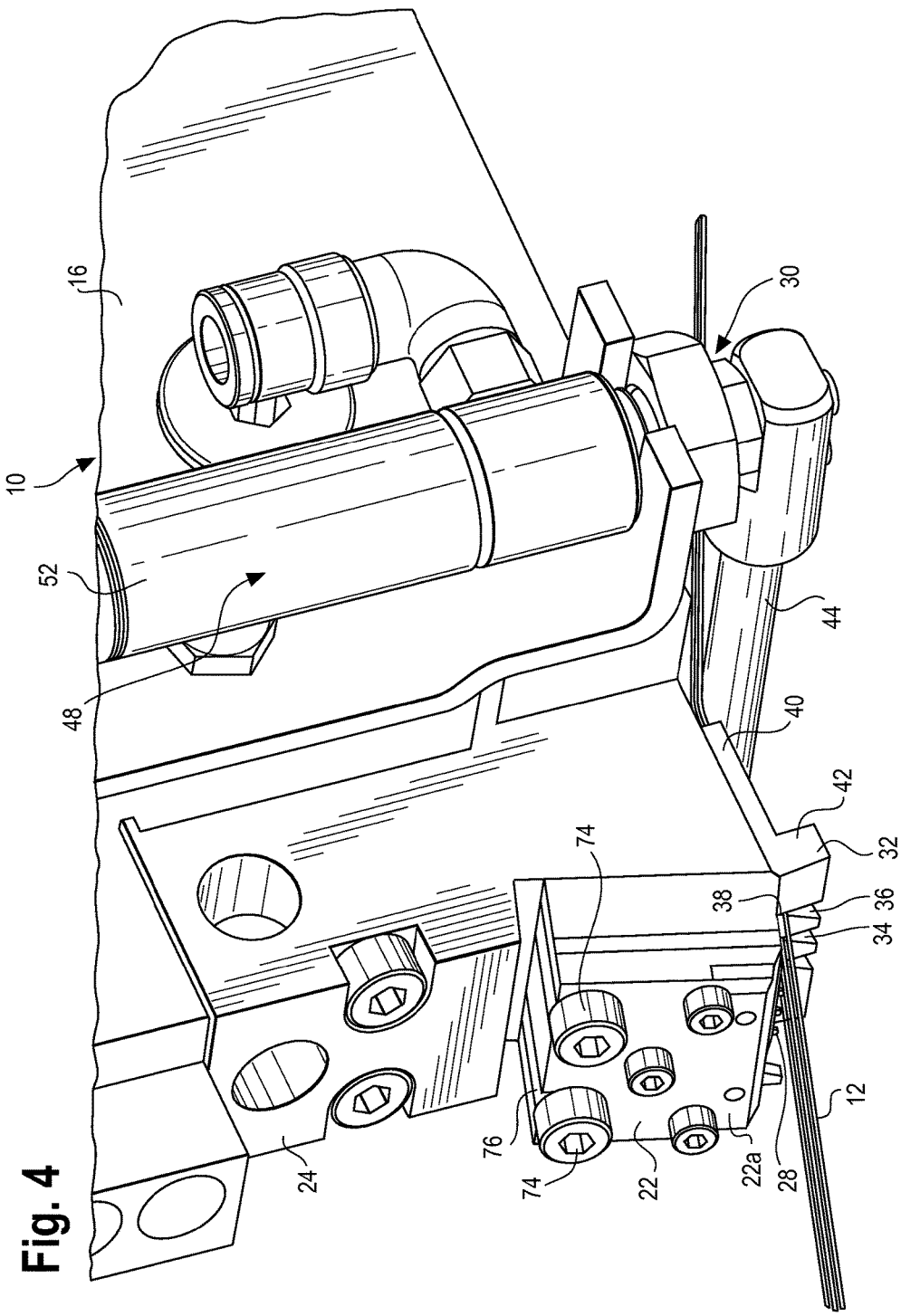
FIG. 4 is a perspective view of a fluid application device having a non-contact nozzle assembly according to an embodiment of the present invention.

FIG. 3 shows the engagement arm 44 in a first position. FIG. 4 is a perspective view of the fluid application device 10 with the engagement arm 44 in a second position. That is, the engagement arm 44 is adjustable between a first position, as shown in FIG. 3, and a second position, as shown in FIG. 4. The first position corresponds to a position where the engagement arm 44 is spaced a first distance from the applicator head 16. The first distance is sufficient to prevent or limit damage, such as burn through, to the strands 12 caused from heat radiating from the applicator head 16 and/or nozzle assembly 22. For example, the engagement arm 44, in the first position may space the strands 12 approximately 3-5 mm from a heat source of the applicator head 16. Moving the engagement arm 44 to, and maintaining the engagement arm 44 in, the first position may be beneficial when the fluid application device 10 is in a static line condition, where the strand are not being fed past the nozzle assembly 22.

The second position corresponds to a position where the engagement arm 44 is spaced a second distance, less than the first distance, from the applicator head 16, such that the strands 12 are moved closer to the applicator head 16 and the respective orifices 28. In one example, the second position of the engagement arm 44 positions the strands approximately 1-3 mm from the orifices 28 of the respective nozzle assembly 22, and more preferably, 1-2 mm. That is, the second position of the engagement arm 44 generally corresponds to the gap G1 over which the first fluid F1 is to be applied on the strand 12. Moving the engagement arm 44 to, and maintaining the engagement arm in, the second position may be beneficial when the fluid application device 10 is in an active line condition, so that the first fluid F1 may be efficiently applied on the strands 12.

Referring still to FIGS. 3 and 4, the engagement arm 44 may be adjusted by an actuating assembly 48. The actuating assembly 48 may be, for example, a pneumatically controlled piston 50 and cylinder 52. For example, the piston 50 may be movable with in a cylinder 52 in response to air or another gas being introduced into the cylinder 52. The piston 50 may be connected directly or indirectly to the engagement arm 44 such that movement of the piston 50 in and out of the cylinder 52 causes the engagement arm 44 to move toward or away from the applicator head 16.

Referring still to FIGS. 3 and 4, the nozzle assembly 22 may be formed as a modular unit. That is, the nozzle assembly 22 may be selectively removed from and secured to the fluid application device 10. For example, the nozzle assembly 22 may be selectively removed from and secured to the applicator head 16, and more specifically, in some embodiments, the adapter 24. Accordingly, the nozzle assembly 22 may be replaced in the event a newer or different nozzle assembly is desired or required. The nozzle assembly 22 is selectively removable from and securable to the fluid application device 10 by way of at least one securing element 74 (FIG. 4). In an exemplary embodiment, the nozzle assembly 22 includes at least one securing opening 76 extending therethrough, each securing opening 76 configured to receive a respective securing element 74.

With further reference to FIGS. 3 and 4, in one embodiment, the nozzle assembly 22 may include two securing openings 76, each configured to receive a respective securing element 74. It is understood that the number of securing openings 76 is not limited to the example above, however. Individual securing openings 76 may be formed as an opening or slot extending through the nozzle assembly 22. The opening or slot may be closed about its periphery or include an open side along an edge of the nozzle assembly 22. The securing elements 74 extend through the securing openings 76 and are received in corresponding bores (not shown) in the fluid application device 10 to secure the nozzle assembly 22 to the applicator head 16. This allows for a modular design of the fluid application device 10 and nozzle assembly 22, such that the nozzle assembly 22 may be replaced without alternations to, or replacement of additional parts on, the fluid application device 10.

In use, the at least one strand 12 may be fed past the nozzle assembly 22, and in particular, past the orifice 28. As described above, the at least one strand 12 extends across the engagement arm 44 of the strand engagement device 30. Movement of the engagement arm 44 by the actuating assembly 48 moves the at least one strand 12 within a corresponding guide slot 34 toward the orifice 28 to a position approximately 0-2 mm from the orifice 28, for application of the adhesive to the strand 12. The actuating assembly 48 may also control the engagement arm 44 to move away from the orifice 28, for example, during a static line condition of the fluid application device 10.

The adhesive may be received in the orifice 28 via the first conduit (not shown) in the nozzle assembly 18. The second fluid F2, or air, may be received in the outlets 29 positioned adjacent to the orifice 28 via a second conduit (not shown). The adhesive is discharged through the orifice 28 for application to the strand of material 12 and the air may be discharged from the outlets 29 to cause the adhesive to oscillate during application, so as to be applied across the strand 12 as the strand is fed by the orifice 28. The adhesive may be discharged from the orifice 28 as a filament for application on the strand 12.

In the examples described above, the strands 12 may be fed by the fluid application device 10 at a higher speed than in traditional non-contact nozzle applications. For example, the strands 12 may be fed past the nozzle assembly 22 at speeds ranging from 400-1000 mpm. In one example, the line speed may be 400-800 mpm, and more particularly, around 700 mpm. This may correspond to a production rate of 1000-1500 products per minute, for example. Compared to traditional non-contact nozzle assembly, the higher line speed in the examples above is a result, in part, of the closer proximity of the strands 12 to the orifices 28. That is, by positioning the strands in close proximity, preferably 0-2 mm from respective orifices 28, the line speed may be increased while still maintaining adequate adhesive application on the strands. That is, by positioning the strands 12 closer to the orifices 28, overspray may be reduced, thereby allowing more efficient application of the first fluid onto the strands 12, which, in turn, allows for the strands 12 to fed through at a higher line speed. Proper positioning of the strands 12 may be assisted by the strand engagement device 30 and the closed ends 38 of the guide slots 34. In addition, the width of the orifices 28 may be increased compared to traditional non-contact configurations to more efficiently apply the first fluid.

As described above, the second fluid F2 may be discharged through the outlets to control application of the first fluid F1, or adhesive, on the strands 12. For example, the second fluid F2 may oscillate the first fluid F1 so that the first fluid F1 is applied on the strands 12 in a substantially sinusoidal pattern. Other patterns may be applied as well by varying the discharge of the second fluid F2. With the sinusoidal pattern, the first fluid F1 is applied over a wider range of the strand 12. In addition, this pattern allows for the strand 12 to be adhered to the substrate 14 at discrete points or segments along the length of the strand, rather than along the entire length of the strand. Accordingly, strand may stretch or relax between the adhered points or segments independently of the substrate 14.

Figure 5:
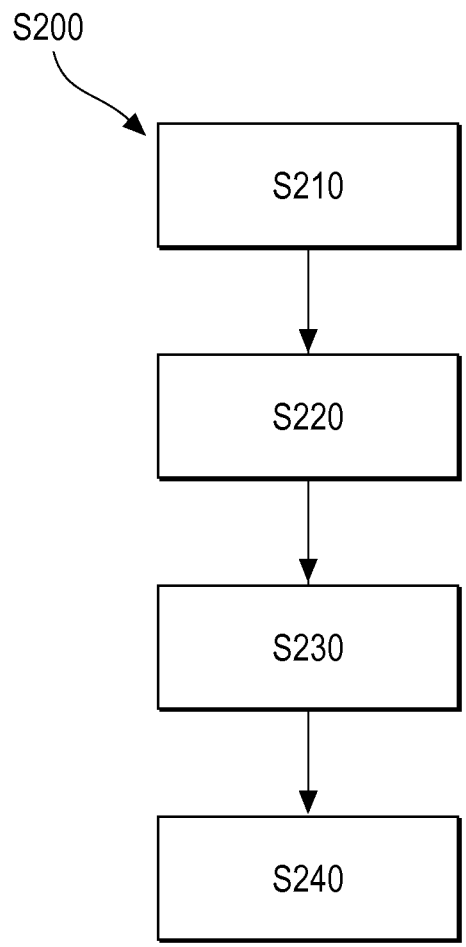
FIG. 5 is a diagram illustrating a method of applying a fluid to an article.

FIG. 5 is a diagram showing a method of applying a first fluid F1, such as an adhesive, to a moving article, such as a strand of material. The method is shown generally at S200 and may be performed at the nozzle assembly 18 described above. In one embodiment, as shown at S210, the method includes positioning the article or strand 12 at the closed end 38 of the guide slot so that the article or strand is spaced a predetermined distance or gap G1 from the orifice 28. The strand 12 may be positioned, for example, at a distance of 1-3 mm, and more preferably, 1-2 mm from the orifice 28. At S220, the article or strand 12 is fed through the guide slot and the past the orifice 28 at a predetermined speed. The strand 24 may be fed by the orifice at speeds up to approximately 1000 mpm. In one embodiment, the article or strand 12 is fed by the orifice 28 at approximately 700 mpm. At S230, the first fluid F1 is applied to the article or strand 12 from the orifice 28. The first fluid F1 may be an adhesive, discharged from the orifice 28 as an adhesive filament. The adhesive may be applied to the strand 12 in a non-contacting manner. At S240, the second fluid F2 may be discharged from at least one outlet 29 adjacent to the orifice 28 to oscillate the first fluid F1, so that the first fluid F1 may be applied all around the strand 12 in a desired pattern. For example, the first fluid F1 may be oscillated by the second fluid F2 to be applied to the strand in a substantially sinusoidal pattern. The first fluid F1 may be applied to the strand or strands 12 with the strand or strands 12 in either of a stretched condition or relaxed condition, depending on a desired application of the substrate, i.e., the nonwoven material or article, to which the strand 12 is to be bonded.

In the embodiments above, the nozzle assembly 22 is formed as a non-contact nozzle assembly. In a non-contact nozzle assembly, the first fluid F1 is discharged from an orifice 28 over a gap to be received on the strand 12. That is, in a non-contact nozzle, the nozzle, and in particular, an orifice discharging a first fluid F1, is spaced from the strand 12 during the fluid application process. In addition, in the non-contact nozzle, the second fluid F2 may be discharged from at least one outlet adjacent to respective orifices 28 of the nozzle assembly 22. The second fluid F2 may be used to control the application of the first fluid F1 on the strand 12, for example, by oscillating the first fluid F1 as it is applied. Accordingly, the first fluid F1 may be applied on the strand 12 in a desired pattern. In addition, by controlling application of the first fluid F1 with the second fluid F2 provides a stitching effect and fluid movement around the strand to provide creep resistance and consistent band retention.

Further, in the examples above, it is understood that the number of strands 12, orifices 28, outlets 29, and guide slots 34 may vary. For example, the fluid application may be able to accommodate anywhere from 1 to 10 strands, but is not limited thereto. For example, the guide plate 32 may include anywhere from 1 to 10 guide slots. A corresponding number of orifices may be provided on the nozzle assembly 22, such that at least one orifice 28 corresponds to, and may be generally aligned with, each guide slot 34. At least one outlet 29 may be provided for each orifice 28 as described above. A strand 12 may be received in each guide slot 34.

The strands 12, coated with the first fluid F1, may be applied and adhered to the substrate 14, i.e., the nonwoven material. The nonwoven material may be used in, for example, manufacture of disposable hygiene products, including but not limited to, baby diapers and pull-on products, adult diapers and incontinence products, feminine hygienic products, medical/hospital pads, light incontinence products, wipes or other nonwoven or film laminated articles used in a hygienic end product using elasticated strands of material.

It should also be understood that various changes and modifications to the presently disclosed embodiments will be apparent to those skilled in the art. Such changes and modifications can be made without departing from the spirit and scope of the present disclosure and without diminishing its intended advantages. It is therefore intended that such changes and modifications be covered by the appended claims.

The invention claimed is:

1. A fluid application device, comprising:
an applicator head; and
a non-contact nozzle assembly fluidly coupled to the applicator head, the non-contact nozzle assembly comprising:
a nozzle body secured to a first surface of the applicator head, the nozzle body having an orifice configured to discharge a first fluid and at least one outlet adjacent to the orifice, the orifice and the at least one outlet are positioned on a common line along a width of the nozzle body, the at least one outlet configured to discharge a second fluid to act on the first fluid discharged from the orifice; and
a guide plate secured to a second surface of the applicator head, different from the first surface, the guide plate having a guide slot spaced from the nozzle body and configured to receive a strand of material, the guide slot having an open end and a closed end; and
a strand engagement device comprising an engagement arm configured to engage the strand of material and to support the strand of material in the guide slot and relative to the applicator head,
wherein the closed end of the guide slot defines a stop configured to space the strand a
predetermined distance from the orifice such that the first fluid is discharged from the orifice over the predetermined distance onto the strand and the predetermined distance is less than 2 mm, and
wherein the guide plate is secured to the applicator head independently of the nozzle body.

2. The fluid application device of claim 1, further comprising more than one guide slot and more than one orifice.

3. The fluid application device of claim 1, further comprising three guide slots and three orifices.

4. The fluid application device of claim 1, wherein the non-contact nozzle assembly further comprises at least one securing opening configured to receive a respective securing element to selectively and releasably secure the non-contact nozzle assembly to the applicator head.

5. The fluid application device of claim 4, wherein the at least one securing opening includes two securing openings.

6. The fluid application device of claim 1, wherein the applicator head further comprises an adapter and the non-contact nozzle assembly is secured to the adapter.

7. The fluid application device of claim 1, wherein the first fluid is an adhesive and the second fluid is air.

8. The fluid application device of claim 1, wherein the orifice has a width of 0.016 to 0.020 inches.

9. The fluid application device of claim 1, wherein the second fluid acts on the first fluid such that the first fluid is applied on the strand in a non-repeating pattern.

10. The fluid application device of claim 1, wherein a width of the guide slot decreases continuously moving toward the applicator head from the open end to the closed end.

11. The fluid application device of claim 1, wherein the strand extends between the stand engagement device and the applicator head such that movement of the strand engagement device toward the applicator head moves the strand toward the applicator head.

12. A non-contact nozzle assembly for a fluid application device for applying at least one fluid to a strand of material, the non-contact nozzle assembly comprising:
a guide plate having a guide slot configured to receive a strand of material, the guide slot having an open end and a closed end;
a nozzle body having an orifice configured to discharge a first fluid onto the strand, wherein the guide slot is configured to be spaced from the nozzle body in a direction of travel of the strand, the nozzle body further having a plurality of outlets positioned adjacent to the orifice, the orifice and plurality of outlets positioned on a common line along a width of the nozzle body, the plurality of outlets configured to discharge a second fluid to control application of the first fluid onto the strand; and
an adapter configured to supply the first fluid and the second fluid to the nozzle body, wherein the nozzle body is configured to be secured to a first surface of the adapter and the guide plate is configured to be secured to a second surface of the adapter, different from the first surface;
wherein the closed end of the guide slot defines a stop configured to space the strand a predetermined distance from the orifice such that the first fluid is discharged from the orifice over the predetermined distance onto the strand and the predetermined distance is less than 2 mm.

13. The non-contact nozzle assembly of claim 12, further comprising more than one guide slot and more than one orifice.

14. The non-contact nozzle assembly of claim 12, further comprising three guide slots and three orifices.

15. The non-contact nozzle assembly of claim 12, the nozzle assembly further comprising at least one securing opening configured to receive a respective securing element to selectively and releasably secure the nozzle assembly to the adapter.

16. The non-contact nozzle assembly of claim 12, wherein the first fluid is an adhesive and the second fluid is air.

17. A fluid application device, comprising:
an applicator head; and
a non-contact nozzle assembly fluidly coupled to the applicator head, the non-contact nozzle assembly comprising:
  a nozzle body secured to a first surface of the applicator head, the nozzle body having an orifice configured to discharge a first fluid and at least one outlet adjacent to the orifice, the at least one outlet configured to discharge a second fluid to act on the first fluid discharged from the orifice; and
  a guide plate secured to a second surface of the applicator head, different from the first surface, the guide plate having a guide slot spaced from the nozzle body and configured to receive a strand of material, the guide slot having an open end and a closed end;
wherein the closed end of the guide slot defines a stop configured to space the strand a predetermined distance from the orifice such that the first fluid is discharged from the orifice over the predetermined distance onto the strand and the predetermined distance is less than 2 mm, and
wherein the second fluid acts on the first fluid such that the first fluid is applied on the strand in a non-repeating pattern.

* * * * *